United States Patent [19]

James

[11] 4,104,464

[45] Aug. 1, 1978

[54] PURIFICATION OF SUCROSE ESTERS

[75] Inventor: Kenneth James, Reading, England

[73] Assignee: Tate & Lyle Limited, London, England

[21] Appl. No.: 677,702

[22] Filed: Apr. 16, 1976

[30] Foreign Application Priority Data

Apr. 18, 1975 [GB] United Kingdom ............... 16216/75
Feb. 13, 1976 [GB] United Kingdom ................ 5795/76

[51] Int. Cl.² ....................... C07H 13/06; C07G 3/00; C11C 3/10
[52] U.S. Cl. ....................................... 536/115; 536/4; 260/410.7
[58] Field of Search .................... 536/4, 115; 260/425, 260/418

[56] References Cited

U.S. PATENT DOCUMENTS 3,141,013 7/1964 O'Boyle .................................. 536/4
3,384,634 5/1968 O'Boyle ............................. 536/115
3,748,324 7/1973 Mizutani et al. ..................... 536/119

Primary Examiner—Henry R. Jiles
Assistant Examiner—Cary Owens
Attorney, Agent, or Firm—Ostrolenk, Faber, Gerb & Soffen

[57] ABSTRACT

A soap-free sucrose ester-containing surfactant is obtained by transesterifying sucrose with at least one fatty acid triglyceride to produce a solid material containing sucrose esters, glycerides and fatty acid soaps, and treating this material with a solution of a metal salt in water or an alkanol to produce a second solid material and separating the soap-free product containing sucrose esters by dissolving the esters present in an alkanol and evaporating the alkanolic solution to dryness. Glycerides are removed, where desired, by extracting with an organic solvent.

16 Claims, No Drawings

PURIFICATION OF SUCROSE ESTERS

This invention relates to the purification of a surface active composition prepared by the transesterification of sucrose with one or more triglycerides.

British Patent Specification No. 1399053 is concerned with a process for the preparation of a surfactant substance which comprises reacting solid particulate sucrose with at least fatty acid triglyceride in the presence of a basic transesterification catalyst at a temperature of from 110° to 140° C at atmospheric pressure and in the absence of any solvent.

The crude product of this process contains the sucrose monoester and diester of the fatty acid; unreacted triglycerides; mono- and di-glycerides of the fatty acid formed as byproducts in the reaction; and fatty acid soaps; together with other minor components and generally some unreacted sucrose, the amount of sucrose depending on the proportions of sucrose and triglycerides used, and the reaction conditions. Products of this type have notable surfactant properties and can be used in an unrefined state for many cleansing purposes. There is a need however for the preparation of relatively pure esters, especially sucrose monoesters, for use as surfactants and emulsifiers in such fields as foodstuffs, fine toiletries, pharmaceuticals, rubber and plastics, paints and brewing.

We have now found that products of this type can be given one or more simple treatments of a solid by a liquid to provide an ester-containing surfactant product relatively free from inorganic materials and sucrose and, depending on the treatments selected, containing a controlled amount of different types of ester.

The crude product, as explained above, contains mono- and di-esters of sucrose with the fatty acid; glycerides; soaps; generally some unreacted sucrose; and coloured impurities and inorganic compounds. A mixture of sucrose esters with soaps is a very useful surfactant material in applications as a cleansing agent; and, for this reason, prior art descriptions of processes which give mixtures of sucrose esters and soaps, for example U.S. Pat. No. 3021324, do not always indicate that the soaps should be removed. However, in some cases soaps are undesirable and it is then necessary to remove them to obtain a soap-free product. For example, a mixture of all the esters present (sucrose esters, mono-, di- and tri-glycerides) is known as "sucrose glycerides" or "sucroglycerides" and is a useful commercial product in its own right, for example, for use in animal feeds. The sucrose esters themselves, especially the monoesters, are also valuable products, as explained above.

Various purification techniques have been proposed for sucrose esters, depending on the reaction medium used to prepare them. These techniques have largely relied on partition between solvents, a technique which is complicated by the efficiency of the desired product as an emulsifier, especially when glycerides are present. In conventional purification methods, the soap present in the reaction mixture is destroyed, generally by acidification, to produce the free fatty acid, e.g. by addition of acetic or citric acid.

Alternatively, as described in UK Patent Specification No. 1295721, the soaps can be decomposed by a double decomposition reaction with metal salt, the resulting mixture being partitioned between two solvents.

We have now found, however, that especially in the presence of glycerides, solvent-solvent partition methods are difficult to handle because of emulsification and require salting out techniques or elevated temperatures in order to be viable. Elevated temperatures are, however, very undesirable when working with inflammable, volatile solvents.

According to the present invention, there is provided a process for the preparation of a sucrose ester-containing surfactant, which comprises transesterifying sucrose with at least one fatty acid triglyceride to form a first solid material containing:

(i) fatty acid mono- and di-esters of sucrose;
(ii) fatty acid mono-, di- and triglyercides; and
(iii) fatty acid soaps;

and subsequently treating said first solid material with a solution of a metal salt in water or in an alkanol containing 1 to 4 carbon atoms, the metal being one which forms fatty acid salts which are insoluble in water or the said alkanol, to produce a second solid material containing said insoluble fatty acid metal salts, and separating a product containing sucrose esters by dissolving the esters present in an alkanol with 1 to 4 carbon atoms and evaporating the alkanolic solution to dryness to give a third solid material.

The metal salt is conveniently a Group 2 or Group 3 metal salt and serves to convert any free fatty acid and/or soaps thereof into insoluble Group 2 or Group 3 metal soaps. Typical Group 2 metals include calcium, magnesium and barium in Group 2a and zinc in Group 2b, calcium being particularly preferred. A typical Group 3 metal salt is an aluminium salt in Group 3a. (All reference to Groups used herein refer to the Periodic Table of the Elements in the Handbook of Chemistry and Physics, 51st edition, published by The Chemical Rubber Co., Ohio, U.S.A.

Naturally, the salt solution should contain sufficient metal salt to convert as much of the soaps into insoluble metal soaps as is desired. Conveniently, when substantially all the soaps are to be removed, an excess of salt, e.g. about 1.5 moles per mole of soap, is used.

Any soluble salt can be used, whether a single salt such as calcium acetate, calcium chloride, zinc acetate, zinc chloride, magnesium sulphate or aluminium sulphate, or a double salt such as aluminium ammonium sulphate. The solvent is conveniently water, or alternatively the above mentioned lower alkanol containing 1 to 4 carbon atoms, such as ethanol (e.g. in the form of industrial methylated spirits) or, better, isopropanol (I.P.A.). The salts, in the case of alkanol solution, should be salts having an appreciable covalent character, such as chlorides or salts of weak organic acids such as acetates. Calcium chloride or zinc acetate are preferred.

Sucrose esters are well known as being particularly efficient as lime-soap dispersing agents. It is perhaps surprising, therefore, that, particularly in aqueous conditions, the formation of insoluble soaps such as lime soaps enables the esters to be easily separated and does not lead to intractable emulsions being formed.

Simple treatment of the mixture with an alcoholic solution of the salt, e.g. calcium chloride in I.P.A., and evaporation of the supernatant liquid separated from the coagulated solids, yields in one stage a "sucrose glycerides" mixture of commercial utility (Product I).

Where the sucrose esters are required to be separated from glycerides present, another treatment, herein referred to as a solvent treatment, is required. In this treatment, one of the solid materials, i.e. the first solid material obtained directly from the transesterification reaction or the second solid material obtained after treatment with a solution of a metal salt, or the third solid material obtained after evaporating the alkanol solution to dryness, is treated with an organic solvent in which glycerides are soluble, but sucrose mono- and di-esters are substantially insoluble. Ketonic solvents such as acetone and methyl ethyl ketone are suitable in this extraction but more preferably a less hydrophilic, water-immiscible solvent is used, for example an ester such as ethyl acetate or a chlorohydrocarbon such as 1,2-dichloroethane. This extraction removes mono-, di- and tri-glycerides, where present in the reaction mixture, and also, where present, the higher esters of sucrose. Any of these esters can be recovered as by-products from the solvent extract.

If the solvent treatment is effected on the first solid material, i.e. the reaction mixture itself, it is followed by the metal salt treatment using a metal salt dissolved in either water or an alcohol.

Aqueous metal salt treatment removes in the liquid phase sucrose, coloured impurities and inorganic materials leaving a solid residue containing the desired esters and precipitated metal salts (Product II). The esters can then be separated by treating this solid with an alcoholic solvent, e.g. I.P.A.

Alcoholic treatment gives an alcoholic solution of the esters and a solid residue of precipitated metal salts. If desired, the ester material thus obtained can be further purified by partitioning between a ketone, such as methyl ethyl ketone, and water to remove coloured impurities and sucrose.

If the above mentioned solvent treatment is effected on the residue after the metal salt treatment using an aqueous solution of the metal salt, it produces a solid residue similar to Product II from which the desired esters can be obtained by alcohol extraction as described for Product II. The solid residue from the metal salt treatment can be filtered off, conveniently on a rotary drum filter. The separation of the insoluble residue is improved if the slurry obtained is gently mixed at a moderately elevated temperature (e.g. up to 70° C, especially 35° to 60° C). This treatment helps to coagulate the solid material so that it can be more easily filtered. The filter cake is preferably dried before being submitted to the solvent treatment.

Thus each of the treatments with a metal salt or a solvent involves a simple extraction of a solid material with a liquid, and thus involves no liquid/liquid extractions with their attendant problems.

The Examples illustrate the invention further (all percentages referred to therein are on a weight basis):-

EXAMPLE 1

50.79 kg of tallow and 6.0 kg of the surfactant product (unpurified) of an earlier similar reaction were mixed in a 200 liter reactor using a four horse power Silverson mixer fitted with a high-shear head operating at 3,000 rpm, while passing steam through an external jacket fitted to the reactor. When the temperature of the resulting suspension reached 125° C, 21.59 kg of sucrose (granulated sugar) and 6.35 kg of anhydrous potassium carbonate were added, and the mixing was continued. The reaction mixture began to thicken after about 1½ hours and after about 5 hours cooling water was circulated through the jacket around the reactor in order to maintain the temperature of the mixture at 125° C. The mixing was stopped after 12 hours and the mixture was allowed to cool and solidify yielding about 83 kg of a waxy surfactant material. This material was found to contain 33% soaps, 13.3% monoglycerides, 12.1% diglycerides, 12.0% sucrose, 17.1% sucrose monoester and about 3% sucrose diester. 1 kg of this material was flaked and added to 2.5 liters of an aqueous solution containing 160g of calcium chloride. The mixture was stirred to produce a slurry of pH 7.4 which was warmed at 35° C for 15 minutes under water-pump vacuum in a rotary evaporator to coagulate the solids and remove some of the water. The mixture was then filtered (sintered glass) and the cake of solids was pressed to remove as much water as possible.

The resulting damp cake was stirred with 2 × 3 liters ethyl acetate. The mixture was allowed to settle and the solvent extract was separated. This extract can be evaporated to yield a waxy residue (approximately 180 g) containing mono-, di- and tri-glycerides which can be purified further as required.

The residue (approximately 500 g) from the ethyl acetate extraction was stirred with 2 × 2 liters isopropanol and the mixture filtered (suction, sintered glass) and the filtrate evaporated to dryness to yield a brown soft waxy material (130 g) containing 80% sucrose monoester and diester together with approximately 10% sucrose, 2.3% monoglyceride and 6.7% soaps.

EXAMPLE 2

200 g of the crude reaction product obtained as described in Example 1 were flaked and added to a solution of calcium chloride (32 g) in water (500 ml). The suspension was stirred at 60° to 70° C to coagulate the solid. The suspension was then filtered, and the solid material was washed with brine (15 g sodium chloride in 250 ml water) and dried.

The dry material was then added to isopropanol (2.6 liters, 45° C) and the mixture was stirred vigorously for 30 minutes. The mixture was then filtered and the filtrate evaporated to dryness. GLC analysis of the residue indicated the following composition: monoglycerides, 18.3%; diglycerides, 18.1%; triglycerides, 5.5%; sucrose monoesters 40.1%; sucrose diesters 18.0%.

EXAMPLE 3

Calcium chloride (13.03 g) was dissolved in isopropanol (3 liters) at 40° C. 200 g of the crude reaction product obtained as described in Example 1 were flaked and added to the warm solution and the mixture was stirred vigorously for 2 hours. The mixture was then filtered and the filtrate evaporated to dryness. GLC analysis of the dried residue indicated the following composition: monoglycerides, 24.56%; diglycerides, 16.31%; triglycerides, 14.32%; sucrose monoesters 37.82%; sucrose diesters 14.34%; sucrose 2.65%.

EXAMPLE 4

200 g of the crude reaction product obtained as described in Example 1 were added to dry 1,2-dichloroethane (3 liters) and the suspension was stirred for 3 hours and allowed to stand over night. The solid was filtered off and dried.

Calcium chloride (13.03 g) was dissolved in isopropanol (2.25 liters) at 40° C. The dried solid was added to the warm isopropanol solution and the suspension was stirred at high speed for 3 hours. The mixture was then filtered and the filtrate evaporated to dryness. GLC analysis of the dried residue indicated the following composition: monoglycerides, 14.24%; soaps, 10.09%;

sucrose monoesters, 49.36%; sucrose diesters 24.63%; sucrose 1.68%.

EXAMPLE 5

1200 g of a dried product obtained by aqueous calcium chloride treatment of a reaction mixture as described in Example 1, but using partially hardened palm oil instead of tallow, were extracted with ethyl acetate (12 liters) to yield an extract which contained 507 g of mixed mono-, di- and tri-glycerides. The residue (693 g) was extracted with hot isopropanol (10 ml/g) to yield sucrose esters (300 g).

EXAMPLE 6

A dried crude product (700 g) obtained as in Example 1 after aqueous calcium chloride treatment, but using partially hardened palm oil instead of tallow, was extracted with hot isopropanol (10 ml/g) to yield 350 g of sucroglycerides.

EXAMPLE 7

A dried crude product (1 kg) obtained as in Example 1 using an aqueous calcium chloride treatment, but using fully hydrogenated palm oil instead of tallow, was extracted with ethyl acetate (10 ml/g) to yield a mixture of mono-, di- and tri-glycerides (390 g). The residue (610 g) was extracted with hot isopropanol (10 ml/g) to yield sucrose esters (290 g).

EXAMPLE 8

The dried crude product used as starting material in Example 7 (1 kg) was extracted with hot isopropanol (10 ml/g) to yield sucroglycerides (600 g).

EXAMPLE 9

The process of Example 7 was repeated using a product (1 kg) derived from fully hydrogenated tallow in place of fully hydrogenated palm oil to give an extract of mono-, di- and triglycerides (400 g). The residue (600 g) was extracted with hot isopropanol (10 ml/g) to yield 270 g of sucrose esters.

EXAMPLE 10

The process of Example 8 was repeated using a product (1 kg) derived from fully hydrogenated tallow in place of fully hydrogenated palm oil to yield 500 g of sucroglycerides.

EXAMPLE 11

200 g of a crude transesterification product obtained as in Example 1 were treated with 50 g of aluminium ammonium sulphate (Al NH$_4$(SO$_4$)2.12H$_2$0) in 2 liters of water at room temperature. The mixture was then filtered and the dark brown dried solids (177 g) were extracted with ethyl acetate and isopropanol as in Example 1 to yield a similar product.

A byproduct of the treatment is an aluminium soap which is of use industrially, e.g. in greases.

EXAMPLE 12

The treatment of Example 11 was repeated, using 30 g of zinc acetate (Zn(OAc)$_2$.2H$_2$0) instead of the aluninium salt. The dried solids (174 g) were extracted with ethyl acetate (2 × 6 ml) and the dark brown dried solid residue (96 g) was extracted with isopropanol as before, to give a similar product.

EXAMPLE 13

The salt treatment of Example 1 was repeated using 200 g of crude reaction product and 32 g calcium chloride in 1 liter of water. The mixture was stirred for 30 minutes at room temperature and then heated to 60° to 70° C to coagulate it. The solids were suspended in one liter of water containing 30 g sodium chloride and coagulated further at 60° to 70° C. The dried solids (177 g) were then halved.

(a) One half of the solids was extracted with industrial methylated spirits (approximately 1.5 liters) to give an extract of sucroglycerides (43 g).

(b) The other half of the solids was extracted with methyl ethyl ketone to remove mixed glycerides in the same way as with ethyl acetate. The residue was extracted with I.P.A. in the usual way to give a similar product.

EXAMPLE 14

The treatment of Example 3 was repeated, using 15.96 g of granular zinc chloride in place of calcium chloride. The mixture was stirred for about 1 hour and filtered. The filtrate was evaporated to give 125 g of sucroglycerides.

EXAMPLE 15

The treatment of Example 11 was repeated, using 32 g of anhydrous magnesium sulphate in place of the aluminium salt. The dried solids were extracted with ethyl acetate and I.P.A. as before to yield a similar product.

I claim:

1. A process for the preparation of a soap-free, sucrose ester-containing surfactant, which comprises transesterifying sucrose with at least one fatty acid triglyceride to form a first solid material containing:
   (i) fatty acid mono- and di-esters of sucrose;
   (ii) fatty acid mono-, di- and tri-glycerides; and
   (iii) fatty acid soaps, and without an intervening distillation treatment, treating said first solid material with a solution of a metal salt in water or in an alkanol containing 1 to 4 carbon atoms, the salt being a salt of a metal selected from those which form fatty acid salts which are insoluble in said solvent to produce a second solid material containing said insoluble fatty acid metal salts, and separating a product containing sucrose esters by dissolving the esters present in an alkanol with 1 to 4 carbon atoms and evaporating the alkanolic solution to dryness to give a third solid material.

2. The process according to claim 1 in which the said salt is a salt of a Group 2 metal.

3. The process according to claim 2 in which said salt is selected from the group consisting of salts of magnesium, calcium, barium and zinc.

4. The process according to claim 3 in which said salt is selected from the group consisting of calcium chloride, calcium acetate, magnesium sulphate, zinc chloride and zinc acetate.

5. The process according to claim 1 in which the said salt is a salt of a Group 3 metal.

6. The process according to claim 5 in which said salt is a salt of aluminium.

7. The process according to claim 6 in which the salt is selected from the group consisting of aluminum sulphate and aluminium ammonium sulphate.

8. The process according to claim 1 in which the alkanol is selected from the group consisting of isopropanol and ethanol.

9. The process according to claim 1 in which the first solid material is treated with an aqueous metal salt solution and the slurry of the solution and the second solid material thereby obtained is mixed at a temperature up to 70° C before the solids are removed.

10. The process according to claim 1 in which a product substantially free from mono-, di- and triglycerides is obtained by extracting one of said solid materials with an organic solvent for glycerides in which sucrose mono- and di-esters are substantially insoluble.

11. The process according to claim 10 in which the first solid material is extracted with said organic solvent before treatment with the metal salt solution.

12. The process according to claim 10 in which the metal salt is dissolved in water and the second solid material is extracted with said organic solvent before selectively dissolving the esters in the alkanol.

13. The process according to claim 10 in which the metal salt is dissolved in water or an alkanol with 1 to 4 carbon atoms and the third solid material is extracted with said organic solvent.

14. The process according to claim 10 in which the organic solvent is selected from the group consisting of ester solvents, ketone solvents and chlorohydrocarbon solvents.

15. The process according to claim 14 in which the organic solvent is selected from the group consisting of ethyl acetate, methyl ethyl ketone and 1,2-dichloroethane.

16. A process for preparing a surfactant, which comprises reacting solid particulate sucrose with at least one triglyceride of a fatty acid having at least 8 carbon atoms, in the presence of a basic transesterification catalyst at a temperature of from 110° to 140° C at atmospheric pressure and in the absence of any solvent; and then (a) treating the crude reaction product with an aqueous salt of a metal capable of forming an insoluble salt (soap) with a fatty acid, and separating the insoluble material;

(b) extracting the separated soluble material with an organic solvent in which glycerides and fatty acids are soluble but sucrose mono- and di-esters are substantially insoluble; and (c) extracting the insoluble residue from (b) with a polar solvent for sucrose mono- and di-esters, but in which fatty acid soaps are substantially insoluble.

* * * * *